(12) United States Patent
Yang et al.

(10) Patent No.: US 10,723,860 B2
(45) Date of Patent: Jul. 28, 2020

(54) ATTRITION-RESISTANT SUPERABSORBENT POLYMER, METHOD FOR PREPARING THE SAME AND COMPOSITION FOR PREPARING THE SAME

(71) Applicant: LG Chem, Ltd., Seoul (KR)

(72) Inventors: Young-In Yang, Daejeon (KR); Young Sam Kim, Daejeon (KR); Bo-Hee Park, Daejeon (KR); Su-Jin Kim, Daejeon (KR)

(73) Assignee: LG Chem, Ltd. (KR)

( * ) Notice: Subject to any disclaimer, the term of this patent is extended or adjusted under 35 U.S.C. 154(b) by 232 days.

(21) Appl. No.: 15/754,481

(22) PCT Filed: Nov. 23, 2016

(86) PCT No.: PCT/KR2016/013557
§ 371 (c)(1),
(2) Date: Feb. 22, 2018

(87) PCT Pub. No.: WO2017/104999
PCT Pub. Date: Jun. 22, 2017

(65) Prior Publication Data
US 2018/0237611 A1  Aug. 23, 2018

(30) Foreign Application Priority Data

Dec. 14, 2015 (KR) .......... 10-2015-0178269
Nov. 7, 2016 (KR) .......... 10-2016-0147386

(51) Int. Cl.
*C08J 9/228* (2006.01)
*C08K 3/36* (2006.01)
*C08K 3/22* (2006.01)
*A61L 15/18* (2006.01)
*A61L 15/20* (2006.01)
*A61L 15/42* (2006.01)
*A61L 15/60* (2006.01)
*A61L 15/24* (2006.01)
*C08J 3/075* (2006.01)
*C08K 5/053* (2006.01)
*C08J 3/24* (2006.01)
*C08K 5/09* (2006.01)
*C08K 5/092* (2006.01)
*C08K 3/10* (2018.01)
*C08K 3/30* (2006.01)
*C08K 3/04* (2006.01)

(52) U.S. Cl.
CPC .............. *C08K 3/36* (2013.01); *A61L 15/18* (2013.01); *A61L 15/20* (2013.01); *A61L 15/24* (2013.01); *A61L 15/425* (2013.01); *A61L 15/60* (2013.01); *C08J 3/075* (2013.01); *C08J 3/24* (2013.01); *C08J 9/228* (2013.01); *C08K 3/10* (2013.01); *C08K 3/22* (2013.01); *C08K 3/30* (2013.01); *C08K 5/053* (2013.01); *C08K 5/09* (2013.01); *C08K 5/092* (2013.01); *C08J 2205/022* (2013.01); *C08J 2333/02* (2013.01); *C08K 3/04* (2013.01); *C08K 2003/2227* (2013.01); *C08K 2003/2241* (2013.01); *C08K 2003/3081* (2013.01); *C08K 2201/002* (2013.01); *C08K 2201/005* (2013.01); *C08K 2201/006* (2013.01); *C08K 2201/014* (2013.01)

(58) Field of Classification Search
CPC .......... A61L 15/18; A61L 15/20; A61L 15/24; A61L 15/425; A61L 15/60; C08J 3/075; C08J 3/24; C08J 3/245; C08J 9/228; C08J 2205/022; C08J 2333/02; C08K 3/04; C08K 3/10; C08K 3/22; C08K 3/30; C08K 3/36; C08K 5/053; C08K 5/09; C08K 5/092; C08K 2003/2227; C08K 2003/2241; C08K 2003/3081; C08K 2201/002; C08K 2201/005; C08K 2201/006; C08K 2201/014
See application file for complete search history.

(56) References Cited

U.S. PATENT DOCUMENTS

| 6,414,214 B1 | 7/2002 | Engelhardt et al. |
| 8,846,823 B2 * | 9/2014 | Nakamura ............... A61L 15/60 502/402 |
| 9,555,393 B2 * | 1/2017 | Lee ..................... B01J 20/28026 |
| 10,471,410 B2 * | 11/2019 | Kim ....................... C08K 5/053 |
| 2006/0204755 A1 | 9/2006 | Torii et al. |

(Continued)

FOREIGN PATENT DOCUMENTS

| CN | 101356202 A | 1/2009 |
| CN | 101932343 A | 12/2010 |

(Continued)

OTHER PUBLICATIONS

Third Party Observation for Application No. PCT/KR2016/013557 dated Apr. 12, 2018.

(Continued)

*Primary Examiner* — John M Cooney
(74) *Attorney, Agent, or Firm* — Lerner, David, Littenberg, Krumholz & Mentlik, LLP (57) ABSTRACT

The present invention relates to an attrition-resistant superabsorbent polymer comprising a superabsorbent polymer; water; and at least three selected from the group consisting of particles having i) a BET specific surface area of 300 to 1500 $m^2/g$ and ii) a porosity of 50% or more, a multivalent metal salt, an organic acid and a polyhydric alcohol, and a preparation method thereof.

20 Claims, 1 Drawing Sheet

(56) References Cited

U.S. PATENT DOCUMENTS

| | | |
|---|---|---|
| 2007/0129517 A1 | 6/2007 | Lang et al. |
| 2008/0032888 A1 | 2/2008 | Nakamura et al. |
| 2009/0191408 A1 | 7/2009 | Tian et al. |
| 2009/0215617 A1 | 8/2009 | Kimura et al. |
| 2009/0298685 A1 | 12/2009 | Torii et al. |
| 2010/0041550 A1 | 2/2010 | Riegel et al. |
| 2010/0130355 A1 | 5/2010 | Tian et al. |
| 2012/0220733 A1 | 8/2012 | Machida et al. |
| 2012/0267570 A1 | 10/2012 | Shi et al. |
| 2013/0026412 A1 | 1/2013 | Machida et al. |
| 2013/0175473 A1 | 7/2013 | Wada et al. |
| 2015/0273433 A1* | 10/2015 | Nakatsuru .............. A61F 13/53 252/194 |
| 2016/0214082 A1 | 7/2016 | Lee et al. |
| 2016/0271584 A1 | 9/2016 | Lee et al. |
| 2017/0050171 A1 | 2/2017 | Yang et al. |
| 2017/0173563 A1 | 6/2017 | Kim et al. |

FOREIGN PATENT DOCUMENTS

| | | |
|---|---|---|
| CN | 103547603 A | 1/2014 |
| EP | 2479195 A1 | 7/2012 |
| EP | 2557095 A1 | 2/2013 |
| JP | 2944447 B2 | 9/1999 |
| JP | 3103754 B2 | 10/2000 |
| JP | 4776969 B2 | 9/2011 |
| JP | 2015107488 A | 6/2015 |
| KR | 20070012731 A | 1/2007 |
| KR | 20110096052 A | 8/2011 |
| KR | 20110133976 A | 12/2011 |
| KR | 20140126821 A | 11/2014 |
| KR | 101507287 B1 | 3/2015 |
| KR | 20150064649 A | 6/2015 |
| KR | 20150064700 A | 6/2015 |
| WO | 98049221 A1 | 11/1998 |
| WO | 2005108472 A1 | 11/2005 |
| WO | 2007037522 A1 | 4/2007 |
| WO | 2007116777 A1 | 10/2007 |
| WO | WO-2011090130 A1 * | 7/2011 ............. A61L 15/60 |
| WO | 2015084060 A1 | 6/2015 |

OTHER PUBLICATIONS

International Search Report for PCT/KR2016/013557 dated Mar. 2, 2017.

* cited by examiner

Immediately after addition of superabsorbent polymers 20 seconds after the addition of superabsorbent polymers

ATTRITION-RESISTANT SUPERABSORBENT POLYMER, METHOD FOR PREPARING THE SAME AND COMPOSITION FOR PREPARING THE SAME

CROSS-REFERENCE TO RELATED APPLICATION(S)

The present application is a national phase entry under 35 U.S.C. § 371 of International Application No. PCT/KR2016/013557, filed on Nov. 23, 2016, which claims priority to and the benefit of Korean Patent Application No. 10-2015-0178269 filed on Dec. 14, 2015, and Korean Patent Application No. 10-2016-0147386, filed on Nov. 7, 2016 with the Korean Intellectual Property Office, the disclosures of which are incorporated herein by reference.

TECHNICAL FIELD

The present invention relates to an attrition-resistant superabsorbent polymer, a method for preparing the attrition-resistant superabsorbent polymer and a composition for preparing the attrition-resistant superabsorbent polymer.

BACKGROUND ART

Superabsorbent polymers (SAPs) are synthetic polymer materials capable of absorbing moisture about 500 to 1000 times their own weight. Due to high moisture-absorbing power, such super absorbent polymers started to be practically applied in sanitary products, and now they are widely used for preparation of various products, for example, hygiene products such as paper diapers for children and adults or the like, water retaining soil products for gardening, water stop materials for the civil engineering and construction, sheets for raising seedling, fresh-keeping agents for food distribution fields, materials for poultice or the like. When the superabsorbent polymers are used for hygiene products, the superabsorbent polymers present in diapers may serve to absorb and maintain urine.

DISCLOSURE

Technical Problem

Meanwhile, in the course of producing diapers by a conventional technique, the superabsorbent polymers are subjected to strong pressure and physical impact. During this process, a problem arises that due to the attrition of the superabsorbent polymers, the physical properties are significantly deteriorated, resulting in the deterioration of performance of the diapers.

The present invention has been made keeping in mind the problems encountered in the art, and an object of the present invention is to provide a superabsorbent polymer having improved attrition resistance which can exhibit absorbency equal to or higher than a conventional superabsorbent polymer, and at the same time, improve an attrition resistance and maintain the improved attrition resistance for a long period of time, so that when the superabsorbent polymer is applied to a final product such as diapers, the deterioration of physical properties due to physical attrition of the superabsorbent polymer, for example, by compression or strong air transfer during the production process of diapers can be minimized, a method for preparing the same and a composition for preparing the same.

Technical Solution

In order to achieve the object above, in one aspect of the present invention, there is provided an attrition-resistant superabsorbent polymer comprising:
a superabsorbent polymer;
water; and
at least three selected from the group consisting of particles having i) a BET specific surface area of 300 to 1500 $m^2/g$ and ii) a porosity of 50% or more, a multivalent metal salt, an organic acid and a polyhydric alcohol.

In another aspect of the present invention, there is provided a method for preparing an attrition-resistant superabsorbent polymer comprising:
adding water; and
at least three selected from the group consisting of particles having the above features i) and ii), a multivalent metal salt, an organic acid and a polyhydric alcohol to a superabsorbent polymer, thus preparing a hydrous superabsorbent polymer.

In still another aspect of the present invention, there is provided a composition for preparing an attrition-resistant superabsorbent polymer comprising water; and at least three selected from the group consisting of particles having the features i) and ii), a multivalent metal salt, an organic acid and a polyhydric alcohol.

Advantageous Effects

According to the present invention, it has an effect of providing a superabsorbent polymer in which attrition resistance is improved and the improved attrition resistance is maintained for a long time, while having physical properties superior or equal to a conventional superabsorbent polymer.

BEST MODE

Hereinafter, the present invention will be described in more detail.

The present invention relates to an attrition-resistant superabsorbent polymer comprising:
a superabsorbent polymer;
water; and
at least three selected from the group consisting of particles having i) a BET specific surface area of 300 to 1500 $m^2/g$ and ii) a porosity of 50% or more, a multivalent metal salt, an organic acid and a polyhydric alcohol.

In one embodiment of the present invention, the particles may be preferably contained in an amount of 0.0001 to 15 parts by weight based on 100 parts by weight of the superabsorbent polymer, more preferably 0.001 to 2.0 parts by weight, and most preferably 0.05 to 0.15 parts by weight based on 100 parts by weight of the superabsorbent polymer.

When the content of the particles is less than the aforementioned range, it may not be sufficient to obtain the expected effect, and when the content exceeds the above range, the particles are used in an excessive amount, which is not economically preferred.

Typically, a superabsorbent polymer has a hydrophilic surface, and because of capillary force, hydrogen bonding, polymeric inter-particular diffusion, or intermolecular Van der Waals force, resulting from water present between particles upon drying after moisture absorption, an irreversible agglomeration may occur. Therefore, since water is essentially used even in the polymerization and surface crosslinking process of the superabsorbent polymer, an agglomeration may occur and so an internal load may increase, and ultimately, it may be a cause of damaging the equipment. Further, since the agglomerated superabsorbent polymers have a large particle size, which are unsuitable for practical use, there is disadvantage in that a deagglomeration process has to be introduced so as to decrease the particle size to an appropriate size. Also, strong force is applied during deagglomeration process, and thus, there existed a problem that the physical properties of the superabsorbent polymers could be deteriorated due to attrition of the superabsorbent polymers.

In order to solve these problems, attempts have been made to introduce a variety of fine particles, which are present on the surface of the superabsorbent polymer and can function to prevent direct agglomeration of the polymer particles. However, when the fine particles were added in an excessive amount, an aglomeration could be prevented, but there existed a disadvantage that the absorbency under pressure of the superabsorbent polymer was decreased.

To solve such problems, the particles introduced in the superabsorbent polymer of the present invention may have a particle size ranging from 2 nm to 50 μm. Further, the particles may have a BET specific surface area of 300 to 1500 $m^2/g$, preferably 500 to 1500 $m^2/g$, and more preferably 600 to 1500 $m^2/g$. Furthermore, the fine particles may have superhydrophobicity with a water contact angle of 125° or more, preferably 135° or more, and more preferably 140° or more. In addition, the particles may have a particle size ranging from 2 nm to 50 μm and superhydrophobicity with a water contact angle of 125° or more.

Moreover, the particles may have a porosity of 50% or more, and preferably 90% or more. As the attrition-resistant superabsorbent polymer uses the particles having the aforementioned features, the effect of water present on the surface of the polymer may decrease, and further as fine particles having porous superhydrophobicity are used, the agglomeration may be remarkably reduced. In addition, even when a relatively small amount of fine particles is used, permeability may be easily increased, and the absorbency under pressure may be readily maintained.

The particles added in the method for preparing a superabsorbent polymer according to the present invention are not limited by its components as long as they are substances having the aforementioned features. Specifically, inorganic oxides, such as silica ($SiO_2$), alumina, titania ($TiO_2$) or carbon, inorganic compounds, organic polymers, ion exchange resins, metals, metal salts, and the like may be used, but are not limited thereto.

Further, as the process of adding the particles, a method of dispersing particles in a monomer solution, adding particles to a hydrogel polymer and then dry mixing them with primarily dried polymer particles, dispersing particles in water or an organic solvent in which a surface crosslinking agent is dissolved upon surface crosslinking, dry mixing particles separately from water or an organic solvent in which a surface crosslinking agent is dissolved upon surface crosslinking, or dry mixing particles with a surface-crosslinked product, etc. may be used, but is not limited thereto.

In another embodiment of the present invention, the water in the attrition-resistant superabsorbent polymer may be preferably contained in an amount of 1.0 to 20.0 parts by weight, more preferably 1.0 to 10.0 parts by weight, and most preferably 2.5 to 7.5 parts by weight based on 100 parts by weight of the superabsorbent polymer and the particles.

When the content of water is less than the above range, it may not be sufficient to obtain attrition resistance, and when the amount exceeds the above range, the surface stickiness of the polymer may be increased, and irreversible agglomeration between the superabsorbent polymer particles may occur, resulting in a decrease in processability of the polymer and changing the particle size at the same time, and thus, a problem may arise that it may not be suitably used as a product.

In the preparation process of a superabsorbent polymer, water is a polymerization medium, and is used in various applications, including facilitating the dispersion of the crosslinking solution during the surface crosslinking process, or the like. Further, residual moisture in the final product functions as an anti-static agent and a plasticizer for resin, and plays a role in suppressing the formation of very small superabsorbent polymer dust in the application process and preventing the attrition of the superabsorbent polymer particles. Generally, however, when water is added even in a small amount to the superabsorbent polymer, the surface stickiness of the polymer may be increased by the water absorbed on the surface thereof, and irreversible agglomeration of the superabsorbent polymer particles may occur. Such increase in stickiness and agglomeration may result in a decrease in processability such as a load increase in the preparation and application processes, consequently increasing the particle size of the superabsorbent polymer, deteriorating the physical properties and the productivity. Such superabsorbent polymers have been studied to date in terms of the polymerization process thereof and enhancements in absorption capacity thereby, and surface crosslinking for increasing the surface properties of the superabsorbent polymer or absorbency under pressure thereof. Furthermore, research is ongoing into changes in the surface properties of the superabsorbent polymer in order to solve some problems, such as to increase permeability or to prevent caking during storage of the superabsorbent polymer (anti-caking), etc.

In the present invention, water is additionally added to the superabsorbent polymer in the above range to increase the water content, and the water functions as a plasticizer to minimize the physical damage of the superabsorbent polymer, thereby simultaneously satisfying high water content and high processability. Thus, when water is added to the superabsorbent polymer, it becomes possible to uniformly contain water without caking phenomenon. Therefore, when the superabsorbent polymer is applied to the final products such as diapers, it is advantageous in that the deterioration of physical properties caused by physical attrition of the superabsorbent polymer, for example, by compression or strong air transfer during the production process of diapers, may be minimized.

In still another embodiment of the present invention, the organic acid is preferably contained in an amount of 0.001 to 5.0 parts by weight based on 100 parts by weight of the superabsorbent polymer, but is not limited thereto.

When the organic acid is contained in the above range, attrition resistance of the superabsorbent polymer is enhanced, and surface hydrophobicity of the superabsorbent polymer caused by containing the particles defined in the present invention can be reduced. In addition, it has an advantage in that a decrease in the absorbency under pressure (AUP) resulting from the use of the particles defined in the present invention can be minimized.

When the organic acid is contained in an amount exceeding the above range, surface stickiness of the superabsorbent polymer (SAP) occurs, and it may impose a negative influence on the particle size during post-treatment and thus is not economically preferable. Further, the anti-caking efficiency is greatly reduced. In contrast, when the organic acid is contained less than the above range, the desired effect cannot be achieved.

The organic acid may be at least one selected from the group consisting of citric acid, oxalic acid, acetic acid, malic acid, malonic acid, gluconic acid, ascorbic acid, tartaric acid, succinic acid, lactic acid, fumaric acid and salicylic acid. Citric acid is preferred because it is economical, safe and environmentally friendly, but is not limited thereto.

In one embodiment of the present invention,
the polyhydric alcohol may be preferably contained in an amount of 0.01 to 5.0 parts by weight based on 100 parts by weight of the superabsorbent polymer, but is not limited thereto.

When the polyhydric alcohol is used, it is used together with water, which substantially reduces the amount of water contained in the superabsorbent polymer, thereby slightly decreasing the reduction of centrifuge retention capacity (CRC). Further, it may reduce absorption rate (measured vortex value) and may help to reduce hydrophobicity. Lastly, it has effects in increasing attrition resistance of the superabsorbent polymer and prolonging the retention period thereof.

When the polyhydric alcohol is contained in an amount exceeding the above range, a caking phenomenon, in which superabsorbent polymers are entangled or form an aggregate, may be induced. In contrast, when the polyhydric alcohol is contained less than the above range, the desired effect cannot be achieved.

The polyhydric alcohol may be at least one selected from the group consisting of propylene glycol, monoethylene glycol, diethylene glycol, triethylene glycol, tetraethylene glycol, polyethylene glycol, monopropylene glycol, 1,3-propanediol, dipropylene glycol, 2,3,4-trimethyl-1,3-pentanediol, polypropylene glycol, glycerol, polyglycerol, 2-butene-1,4-diol, 1,4-butanediol, 1,3-butanediol, 1,5-pentanediol, 1,6-hexanediol and 1,2-cyclohexanedimethanol. Propylene glycol is preferred because it is economical and safe, but is not limited thereto.

Further, the present invention relates to a method for preparing an attrition-resistant superabsorbent polymer comprising:

adding water; and at least three selected from the group consisting of particles having i) a BET specific surface area of 300 to 1500 $m^2/g$ and ii) a porosity of 50% or more, a multivalent metal salt, an organic acid and a polyhydric alcohol to a superabsorbent polymer, thus preparing a hydrous superabsorbent polymer.

In one embodiment of the present invention, the particles may be preferably contained in an amount of 0.0001 to 15 parts by weight based on 100 parts by weight of the superabsorbent polymer, more preferably 0.001 to 2.0 parts by weight, and most preferably 0.05 to 0.15 parts by weight based on 100 parts by weight of the superabsorbent polymer.

When the content of the particles is less than the aforementioned range, it may not be sufficient to obtain the expected effect, and when the content exceeds the above range, the particles are used in an excessive amount, and thus it is not economically preferred.

Typically, a superabsorbent polymer has a hydrophilic surface, and because of capillary force, hydrogen bonding, polymeric inter-particular diffusion, or intermolecular Van der Waals force, resulting from water present between the particles upon drying after moisture absorption, an irreversible agglomeration may occur. Therefore, since water is essentially used even in the polymerization and surface crosslinking process of the superabsorbent polymers, an agglomeration may occur and so an internal load may increase, and ultimately, it may be a cause of damaging the equipment. Further, since the agglomerated superabsorbent polymers have a large particle size, which are unsuitable for practical use, there is disadvantage in that a deagglomeration process has to be introduced so as to decrease the particle size to an appropriate size. Also, strong force is applied during the deagglomeration process, and thus, there existed a problem that the physical properties of the superabsorbent polymers could be deteriorated due to attrition of the superabsorbent polymers.

In order to solve these problems, attempts have been made to introduce a variety of fine particles, which are present on the surface of the superabsorbent polymer and can function to prevent direct agglomeration of the polymer particles. In the case where the fine particles were added in an excessive amount, agglomeration could be prevented, but there existed a disadvantage that the absorbency under pressure of the superabsorbent polymer was decreased.

To solve such problems, the particles introduced in the superabsorbent polymer of the present invention may have a particle size ranging from 2 nm to 50 μm. Further, the particles may have a BET specific surface area of 300 to 1500 $m^2/g$, preferably 500 to 1500 $m^2/g$, and more preferably 600 to 1500 $m^2/g$. Furthermore, the fine particles may have superhydrophobicity with a water contact angle of 125° or more, preferably 135° or more, and more preferably 140° or more. In addition, the particles may have a particle size ranging from 2 nm to 50 μm and superhydrophobicity with a water contact angle of 125° or more.

Moreover, the particles may have a porosity of 50% or more, and preferably 90% or more. As the attrition-resistant superabsorbent polymer uses the particles having the aforementioned features, the effect of water present on the surface of the polymer may decrease, and further as fine particles having porous superhydrophobicity are used, the agglomeration may be remarkably reduced. In addition, even when a relatively small amount of fine particles is used, permeability may be easily increased, and the absorbency under pressure may be readily maintained.

The particles added in the method for preparing a superabsorbent polymer according to the present invention are not limited by its components as long as they are substances having the aforementioned features. Specifically, inorganic oxides, such as silica ($SiO_2$), alumina, titania ($TiO_2$) or carbon, inorganic compounds, organic polymers, ion exchange resins, metals, metal salts, and the like may be used, but are not limited thereto.

Further, as the process of adding the particles, a method of dispersing particles in a monomer solution, adding particles to a hydrogel polymer and then dry mixing them with primarily dried polymer particles, dispersing particles in water or an organic solvent in which a surface crosslinking agent is dissolved upon surface crosslinking, dry mixing particles separately from water or an organic solvent in which a surface crosslinking agent is dissolved upon surface crosslinking, or dry mixing particles with a surface-crosslinked product, etc. may be used, but is not limited thereto.

In another embodiment of the present invention, the water in the attrition-resistant superabsorbent polymer may be preferably contained in an amount of 0.1 to 20.0 parts by weight, more preferably 1.0 to 10.0 parts by weight, and most preferably 2.5 to 7.5 parts by weight based on 100 parts by weight of the superabsorbent polymer and the particles.

When the content of water is less than the above range, it may not be sufficient to obtain attrition resistance, and when the amount exceeds the above range, the surface stickiness of the polymer may be increased, and irreversible agglomeration between the superabsorbent polymer particles may occur, resulting in a decrease in processability of the polymer and changing the particle size at the same time, and thus, a problem may arise that it may not be suitably used as a product.

In the preparation process of a superabsorbent polymer, water is a polymerization medium, and is used in various applications, including facilitating the dispersion of the crosslinking solution during the surface crosslinking process, or the like. Further, residual moisture in the final product functions as an anti-static agent and a plasticizer for resin, and plays a role in suppressing the formation of very small superabsorbent polymer dust in the application process and preventing attrition of the superabsorbent polymer particles. Generally, however, when water is added even in a small amount to the superabsorbent polymer, the surface stickiness of the polymer may be increased by the water absorbed on the surface thereof, and irreversible agglomeration of the superabsorbent polymer particles may occur. Such increase in stickiness and agglomeration may result in a decrease in processability such as a load increase in the preparation and application processes, consequently increasing the particle size of the superabsorbent polymer, deteriorating the physical properties and the productivity. Such superabsorbent polymers have been studied to date in terms of the polymerization process thereof and enhancements in absorption capacity thereby, and surface crosslinking for increasing the surface properties and absorbency under pressure of the superabsorbent polymer. Furthermore, research is ongoing into changes in the surface properties of the superabsorbent polymer in order to solve some problems, such as to increase permeability or to prevent caking during storage of the superabsorbent polymer (anti-caking), etc.

In the present invention, water is additionally added to the superabsorbent polymer in the above range to increase the water content, and the water functions as a plasticizer to minimize the physical damage of the superabsorbent polymer, thereby simultaneously satisfying high water content and high processability. Thus, when water is added to the superabsorbent polymer, it becomes possible to uniformly contain water without caking phenomenon. Therefore, when the superabsorbent polymer is applied to the final products such as diapers, it is advantageous in that the deterioration of physical properties caused by physical attrition of the superabsorbent polymer, for example, by compression or strong air transfer during the production process of diapers, may be minimized.

In still another embodiment of the present invention,
the organic acid is preferably contained in an amount of 0.001 to 5.0 parts by weight based on 100 parts by weight of the superabsorbent polymer, but is not limited thereto.

When the organic acid is contained in the above range, attrition resistance of the superabsorbent polymer is enhanced, and surface hydrophobicity of the superabsorbent polymer caused by containing the particles defined in the present invention can be reduced. In addition, it has an advantage in that the decrease in the absorbency under pressure (AUP) resulting from the use of the particles defined in the present invention can be minimized.

When the organic acid is contained in an amount exceeding the above range, surface stickiness of the superabsorbent polymer (SAP) occurs, and it may impose a negative influence on the particle size during post-treatment and thus is not economically preferable. Further, the anti-caking efficiency is greatly reduced. In contrast, when the organic acid is contained less than the above range, the desired effect cannot be achieved.

The organic acid may be at least one selected from the group consisting of citric acid, oxalic acid, acetic acid, malic acid, malonic acid, gluconic acid, ascorbic acid, tartaric acid, succinic acid, lactic acid, fumaric acid and salicylic acid. Citric acid is preferred because it is economical, safe and environmentally friendly, but is not limited thereto.

In one embodiment of the present invention,
the polyhydric alcohol may be preferably contained in an amount of 0.01 to 5.0 parts by weight based on 100 parts by weight of the superabsorbent polymer, but is not limited thereto.

When the polyhydric alcohol is used, it is used together with water, which substantially reduces the amount of water contained in the superabsorbent polymer, thereby slightly decreasing the reduction of centrifuge retention capacity (CRC). Further, it may reduce absorption rate (measured vortex value) and may help to reduce hydrophobicity. Lastly, it has effects in increasing attrition resistance of the superabsorbent polymer and prolonging the retention period thereof.

When the polyhydric alcohol is contained in an amount exceeding the above range, a caking phenomenon, in which superabsorbent polymers are entangled or form an aggregate, may be induced. In contrast, when the polyhydric alcohol is contained less than the above range, the desired effect cannot be achieved.

The polyhydric alcohol may be at least one selected from the group consisting of propylene glycol, monoethylene glycol, diethylene glycol, triethylene glycol, tetraethylene glycol, polyethylene glycol, monopropylene glycol, 1,3-propanediol, dipropylene glycol, 2,3,4-trimethyl-1,3-pentanediol, polypropylene glycol, glycerol, polyglycerol, 2-butene-1,4-diol, 1,4-butanediol, 1,3-butanediol, 1,5-pentanediol, 1,6-hexanediol and 1,2-cyclohexanedimethanol. Propylene glycol is preferred because it is economical and safe, but is not limited thereto.

In one embodiment of the present invention, the superabsorbent polymer is prepared by a method comprising:
a) carrying out a thermal polymerization or a photopolymerization of a monomer composition including a water-soluble ethylenically unsaturated monomer and a polymerization initiator to prepare a hydrogel polymer;
b) drying the hydrogel polymer;
c) milling the dried hydrogel polymer to obtain super absorbent polymer particles;
d) adding a surface crosslinking agent to the superabsorbent polymer particles to carry out a surface crosslinking reaction.

For reference, as used herein, the term "superabsorbent polymer particles" refers to particles obtained by drying and milling the hydrogel polymer. More specifically, the hydrogel polymer is a material in a hard jelly form with a size of 1 cm or more and containing water in a large amount (50% or more) after completion of the polymerization. The superabsorbent polymer particles are obtained by drying and milling the hydrogel polymer in a powder form. Thus, the hydrogel polymer corresponds to an intermediate state of the process.

First, the superabsorbent polymer used herein undergoes a step of carrying a thermal polymerization or a photopolymerization of a monomer composition including a water-soluble ethylenically unsaturated monomer and a polymerization initiator to prepare a hydrogel polymer.

To prepare the superabsorbent polymer of the present invention, a polymer may be prepared by steps and methods typically used in the art. Specifically, in the preparation of a superabsorbent polymer of the present invention, the monomer composition includes a polymerization initiator. Depending on the polymerization method, when photopolymerization is carried out, a photopolymerization initiator is used, and when thermal polymerization is carried out, a thermal polymerization initiator is used. However, even when photopolymerization is carried out, a predetermined amount of heat is generated due to irradiation such as UV irradiation, and also some heat is generated through the polymerization reaction, which is an exothermic reaction, and thus a thermal polymerization initiator may be additionally included.

The thermal polymerization initiator used in the preparation method of the superabsorbent polymer according to the present invention is not particularly limited, but preferably includes at least one selected from the group consisting of a persulfate-based initiator, an azo-based initiator, hydrogen peroxide and ascorbic acid. Specifically, examples of the persulfate-based initiator may include sodium persulfate ($Na_2S_2O_8$), potassium persulfate ($K_2S_2O_8$), ammonium persulfate (($NH_4)_2S_2O_8$) and the like, and examples of the azo-based initiator may include 2,2-azobis(2-amidinopropane) dihydrochloride, 2,2-azobis-(N,N-dimethylene)isobutyramidine dihydrochloride, 2-(carbamoylazo)isobutylonitrile, 2,2-azobis[2-(2-imidazolin-2-yl)propane] dihydrochloride, 4,4-azobis-(4-cyanovaleric acid) and the like.

Further, the photopolymerization initiator used in the preparation method of the superabsorbent polymer according to the present invention is not particularly limited, but preferably includes at least one selected from the group consisting of benzoin ether, dialkyl acetophenone, hydroxyl alkylketone, phenyl glyoxylate, benzyl dimethyl ketal, acyl phosphine and a-aminoketone. Meanwhile, specific examples of the acyl phosphine may include commercially available lucirin TPO, that is, 2,4,6-trimethyl-benzoyl-trimethyl phosphine oxide.

Furthermore, in the method for preparing a superabsorbent polymer according to the present invention, the water-soluble ethylenically unsaturated monomer is not particularly limited so long as it is a monomer typically used in the preparation of a superabsorbent polymer, and preferably includes at least one selected from the group consisting of an anionic monomer and a salt thereof, a nonionic hydrophilic monomer, and an amino group-containing unsaturated monomer and a quaternary salt thereof. Specifically, at least one selected from the group consisting of anionic monomers and salts thereof such as acrylic acid, methacrylic acid, maleic anhydride, fumaric acid, crotonic acid, itaconic acid, 2-acryloylethanesulfonic acid, 2-methacryloylethanesulfonic acid, 2-(meth)acryloylpropanesulfonic acid or 2-(meth)acrylamide-2-methylpropane sulfonic acid; non-ionic hydrophilic monomers such as (meth)acrylamide, N-substituted (meth)acrylate, 2-hydroxyethyl(meth)acrylate, 2-hydroxypropyl(meth)acrylate, methoxypolyethyleneglycol (meth)acrylate or polyethyleneglycol (meth)acrylate; and amino group-containing unsaturated monomers and quaternary salts thereof such as (N,N)-dimethylaminoethyl (meth)acrylate and (N,N)-dimethylaminopropyl (meth)acrylamide may be preferably used. More preferably, acrylic acid or salts thereof may be used. When acrylic acid or salts thereof are used as the monomer, there is an advantage in that a superabsorbent polymer having improved absorbency may be obtained.

In addition, in the method for preparing a superabsorbent polymer according to the present invention, in order to impart an effect in accordance with recycling of resources, fine powder in the prepared superabsorbent polymer powder, that is, a polymer or resin powder having a particle size of less than 150 μm may be incorporated in a predetermined amount in the monomer composition. Specifically, a polymer or resin powder having a particle size of less than 150 μm may be added before the initiation of the polymerization of the monomer composition, or in the early, middle or late stages after the initiation of polymerization. At this time, the amount thereof that can be added is not limited, but is preferably added in an amount of 1 to 10 parts by weight based on 100 parts by weight of the monomer contained in the monomer composition in order to prevent the deterioration of physical properties of the finally prepared superabsorbent polymer.

Meanwhile, in the method for preparing a superabsorbent polymer according to the present invention, the concentration of the water-soluble ethylenically unsaturated monomer in the monomer composition may be appropriately determined and used in consideration of the polymerization time and the reaction conditions, and it may preferably be 40 to 55% by weight. When the concentration of the water-soluble ethylenically unsaturated monomer is less than 40% by weight, it may be disadvantageous in view of economy. When the concentration thereof exceeds 55% by weight, the milling efficiency of the polymerized hydrogel polymer during milling may decrease.

The method for preparing hydrogel by carrying out a thermal polymerization or a photopolymerization of the monomer composition as described above is not limited by its constitution so long as it is a polymerization method typically used in the art. Specifically, polymerization methods are largely classified into thermal polymerization and photopolymerization, depending on the polymerization energy source. Typically, the thermal polymerization may be carried out using a reactor having a stirring spindle, such as a kneader, and the photopolymerization may be carried out using a reactor equipped with a movable conveyor belt. However, the polymerization methods described above are merely illustrative, and the present invention is not limited to these polymerization methods.

For example, as described above, a hydrogel polymer obtained by providing hot air to a reactor like a kneader equipped with the agitating spindles, or heating the reactor, and carrying out a thermal polymerization, which is then discharged through the outlet of the reactor, may have a size ranging from several cm to several mm, depending on the type of agitating spindles equipped in the reactor. Specifically, the size of the hydrogel polymer may vary depending on the concentration of the monomer mixture to be injected thereto, the injection speed, or the like, and the hydrogel polymer having an average particle diameter of about 2 to 50 mm may be generally obtained.

In addition, as described above, when photopolymerization is carried out using a reactor equipped with a movable conveyor belt, a typically obtained hydrogel polymer may be a hydrogel polymer in the form of a sheet having a width of the belt. At this time, the thickness of the polymer sheet may vary depending on the concentration of the monomer composition to be injected thereto, and the injection speed thereof, but the monomer composition is preferably provided so as to obtain a typical polymer sheet having a thickness of 0.5 to 5 cm. In the case where the monomer composition is provided to an extent that the thickness of the sheet polymer is too thin, it is not preferable due to low production efficiency. In contrast, when the thickness of the polymer sheet is greater than 5 cm, the polymerization reaction may not be uniformly carried out throughout the entire thickness, due to excessively thick thickness.

The light source which can be used in the photopolymerization step is not particularly limited, and any UV light source may be used without particular limitation so long as it is known to trigger a photopolymerization reaction. For example, a light having a wavelength of about 200 to 400 nm may be used, and a UV light source such as a Xe lamp, a mercury lamp or a metal halide lamp may be used. Further, the photopolymerization step may be carried out at an intensity ranging from about 0.1 mw/cm$^2$ to about 1 kw/cm$^2$ for about 5 seconds to about 10 minutes. When the intensity of light applied to the photopolymerization reaction and the time thereof are excessively small and short, sufficient polymerization may not occur. In contrast, when they are excessively large and long, the quality of the superabsorbent polymer may be deteriorated.

Subsequently, in step b), a step of drying the hydrogel polymer is performed.

The hydrogel polymer obtained in step a) typically has a water content of 30 to 60% by weight. As used herein, the term "water content" refers to a value obtained by subtracting the weight of polymer in a dried state from the weight of hydrogel polymer as water content occupied, based on the total weight of the hydrogel polymer. (Specifically, it is defined as a value calculated by measuring weight loss of the polymer due to the evaporation of moisture while drying the polymer by raising the temperature of the polymer via IR heating. At this time, the drying is performed in such a manner that the temperature is raised from room temperature to 180° C. and then maintained at 180° C., and the total drying time is set to 20 minutes, including 5 minutes of raising the temperature, thereby measuring the water content.)

The hydrogel polymer obtained in step a) undergoes a drying step, and the drying temperature of the drying step may be 150° C. to 250° C. As used herein, the term "drying temperature" may be defined as the temperature of a heat medium supplied for the drying process, or the temperature of a drying reactor containing a heat medium and a polymer in the drying process.

When the drying temperature is less than 150° C., the drying time may become excessively long, and the physical properties of the finally formed superabsorbent polymer may be deteriorated. In contrast, when the drying temperature is higher than 250° C., only the surface of the polymer may be excessively dried, and thus fine powder may be formed in the subsequent milling process, and the physical properties of the finally formed superabsorbent polymer may be deteriorated. The drying is preferably carried out at a temperature of 150° C. to 250° C., and more preferably at 160° C. to 200° C.

Meanwhile, the drying time is not limited, but the drying may be carried out for 20 to 90 minutes, in consideration of processing efficiency or the like.

Further, the drying process of the drying step can also be used without limitation in its constitution, so long as it is typically used as a drying process of hydrogel polymers. Specifically, the drying step may be performed by hot air supply, IR irradiation, microwave irradiation or UV irradiation, etc. The polymer after the drying process may have a water content of 0.1 to 10% by weight.

Meanwhile, the method for preparing the superabsorbent polymer according to the present invention may further include simple milling step before the drying step, as needed, in order to increase efficiency of the drying step. The simple milling step before the drying step is carried out so that the particle size of the hydrogel polymer falls in the range of 1 to 15 mm. To mill the polymer to have a particle size of less than 1 mm is technically difficult due to the high water content of the hydrogel polymer, and the milled particles may agglomerate together. In contrast, when the polymer is milled to have a particle size larger than 15 mm, the effect of increasing the efficiency of the subsequent drying step by the milling process may be insignificant.

In the simple milling step before the drying step, the milling device used is not limited in its constitution. Specifically, examples thereof may include any one milling device selected from the group consisting of a vertical pulverizer, a turbo cutter, a turbo grinder, a rotary cutter mill, a cutter mill, a disc mill, a shred crusher, a crusher, a chopper, and a disc cutter, but the mill is not limited to the examples described above.

When the milling step is performed to increase the drying efficiency before the drying step, the polymer, which has high water content, may adhere to the surface of the mill. Thus, in order to increase the efficiency of the milling step before drying the hydrogel polymer, an additive or the like capable of preventing adhering upon milling may be further used. Specifically, the type of additives that can be used is not limited in its constitution, and examples thereof may include a fine powder agglomeration inhibitor, such as steam, water, a surfactant, and inorganic powder, such as clay or silica; a thermal polymerization initiator, such as a persulfate-based initiator, an azo-based initiator, hydrogen peroxide, and ascorbic acid; and a crosslinking agent, such as an epoxy-based crosslinking agent, a diol-based crosslinking agent, a crosslinking agent containing a bifunctional or trifunctional or higher polyfunctional acrylate, and a monofunctional compound having a hydroxyl group, but the additives are not limited to the examples described above.

After the drying step, the method for preparing the superabsorbent polymer according to the present invention undergoes step c) of milling the dried hydrogel polymer to obtain superabsorbent polymer particles. The superabsorbent polymer particles obtained after the milling step may have a particle size of 150 to 850 μm. In the method for preparing a superabsorbent polymer according to the present invention, the milling device used for milling the particles to have the particle size may specifically include a pin mill, a hammer mill, a screw mill, a roll mill, a disc mill, or a jog mill, but is not limited thereto.

Subsequently, in step d), a surface crosslinking agent is added to the superabsorbent polymer particles to carry out surface crosslinking reaction. In step above, the surface crosslinking agent is added, and the composition of the surface crosslinking agent added to each of the superabsorbent polymer particles may be the same, or a different composition may be added as needed, depending on the particle size thereof.

The surface crosslinking agent added in the method for preparing a superabsorbent polymer according to the present invention is not limited in its constitution, so long as it is able to react with a functional group of the polymer. In order to improve the properties of the produced superabsorbent polymer, the surface crosslinking agent may preferably include at least one selected from the group consisting of a polyhydric alcohol compound; an epoxy compound; a polyamine compound; a haloepoxy compound; a condensation product of haloepoxy compound; an oxazoline compound; a mono-, di- or poly oxazolidinone compound; a cyclic urea compound; a multivalent metal salt; and an alkylene carbonate compound.

Specifically, examples of the polyhydric alcohol compound may include at least one selected from the group consisting of mono-, di-, tri-, tetra- or polyethylene glycol, monopropylene glycol, 1,3-propanediol, dipropylene glycol, 2,3,4-trimethyl-1,3-pentanediol, polypropylene glycol, glycerol, polyglycerol, 2-butene-1,4-diol, 1,4-butanediol, 1,3-butanediol, 1,5-pentanediol, 1,6-hexanediol, and 1,2-cyclohexanedimethanol.

Further, examples of the epoxy compound may include ethylene glycol diglycidyl ether and glycidol, etc., and examples of the polyamine compound may include at least one selected from the group consisting of ethylene diamine, diethylene triamine, triethylene tetramine, tetraethylene pentamine, pentaethylene hexamine, polyethyleneimine, and polyamidepolyamine.

Furthermore, examples of the haloepoxy compound may include epichlorohydrin, epibromohydrin and α-methyl epichlorohydrin. Meanwhile, examples of the mono-, di- or polyoxazolidinone compound may include 2-oxazolidinone or the like.

In addition, examples of the alkylene carbonate compound may include ethylene carbonate or the like. These compounds may be used alone or in combination. Meanwhile, in order to increase the efficiency of the surface crosslinking process, among these surface crosslinking agents, the surface crosslinking agents may be preferably used by containing at least one polyhydric alcohol compound, and more preferably, a polyhydric alcohol compound having 2 to 10 carbon atoms may be used.

In addition, the amount of the surface crosslinking agent added for the surface treatment of the polymer particles by mixing the surface crosslinking agent as described above may be appropriately determined depending on the type of the surface crosslinking agent specifically added or the reaction conditions, and it may be used in an amount of 0.001 to 5 parts by weight, preferably 0.01 to 3 parts by weight, and more preferably 0.05 to 2 parts by weight, based on 100 parts by weight of the typical milled superabsorbent polymer particles.

When the amount of the surface crosslinking agent is too small, the surface crosslinking reaction does not readily occur. In contrast, when the amount thereof exceeds 5 parts by weight based on 100 parts by weight of the polymer, the physical properties of the superabsorbent polymer may rather deteriorate due to excessive surface crosslinking reactions.

At this time, the method of adding the surface crosslinking agent to the polymer is not limited in its constitution. Methods such as adding and mixing the surface crosslinking agent and the polymer powder in a reaction bath, spraying the surface crosslinking agent onto the polymer powder, or mixing by continuously supplying the polymer and the crosslinking agent in a reaction bath, such as a mixer, which operates continuously, may be used.

Further, the surface temperature of the polymer in the step of adding the surface crosslinking agent is preferably 60° C. to 90° C.

Furthermore, according to one embodiment of the present invention, the temperature of the polymer itself may be preferably 20° C. to 80° C. when adding the surface crosslinking agent, in order to raise the temperature to the reaction temperature for the surface crosslinking reaction within 1 to 60 minutes after adding the surface crosslinking agent. In order to realize the above temperature of the polymer, a process that is carried out after the drying step, which is carried out at a relatively high temperature, is continuously performed, and the processing time may be shortened. Alternatively, the polymer may be heated separately when it is difficult to shorten the processing time.

In addition, in the method for preparing a superabsorbent polymer according to the present invention, the surface crosslinking agent itself added to the polymer may be heated so as to raise the temperature to the reaction temperature for the surface crosslinking reaction within 1 to 60 minutes after adding the surface crosslinking agent.

Meanwhile, the method for preparing a superabsorbent polymer according to the present invention is capable of improving efficiency of the surface crosslinking process when carrying out the surface crosslinking reaction after raising the temperature to the reaction temperature for the surface crosslinking reaction within 1 minute to 60 minutes. Consequently, a superabsorbent polymer having excellent physical properties may be obtained while minimizing the content of residual monomer of the finally obtained superabsorbent polymer. Herein, the temperature of the added surface crosslinking agent may be adjusted to 5° C. to 60° C., and more preferably to 10° C. to 40° C. When the temperature of the surface crosslinking agent is lower than 5° C., the effect of reducing the rate of raising a temperature to the temperature of the surface crosslinking reaction obtained by raising the temperature of the surface crosslinking agent is insignificant. In contrast, when the temperature of the surface crosslinking agent is higher than 60° C., the surface crosslinking agent may not be uniformly dispersed in the polymer. As used herein, the surface crosslinking reaction temperature may be defined as the combined temperature of the polymer and the surface crosslinking agent that is added for the crosslinking reaction.

Further, the means for raising the temperature for the surface crosslinking reaction is not limited in its constitution. Specifically, a heating medium may be supplied, or direct heating may be used by means of electricity or the like, however, the present invention is not limited to the examples described above. Specific examples of a heat source that can be used may include steam, electricity, UV rays, IR rays and the like, and in addition, a heated thermal fluid or the like may be used.

Meanwhile, in the method of preparing a superabsorbent polymer according to the present invention, the crosslinking reaction may be carried out for 1 to 60 minutes, preferably 5 to 40 minutes, and most preferably 10 to 20 minutes after raising the temperature for the crosslinking reaction. When the crosslinking reaction time is less than 1 minute, which is excessively short, sufficient crosslinking reaction may not occur. In contrast, when the crosslinking reaction time is longer than 60 minutes, the physical properties of the superabsorbent polymer may rather deteriorate due to the excessive surface crosslinking reaction, and attrition of the polymer may occur due to long-term retention in the reactor.

In addition, the present invention relates to a composition for preparing an attrition-resistant superabsorbent polymer comprising:

water; and at least three selected from the group consisting of particles having i) a BET specific surface area of 300 to 1500 $m^2/g$ and ii) a porosity of 50% or more, a multivalent metal salt, an organic acid and a polyhydric alcohol.

In one embodiment of the present invention, the particles may be preferably contained in an amount of 0.0001 to 15 parts by weight based on 100 parts by weight of the superabsorbent polymer, more preferably 0.001 to 2.0 parts by weight, and most preferably 0.05 to 0.15 parts by weight based on 100 parts by weight of the superabsorbent polymer.

When the content of the particles is less than the aforementioned range, it may not be sufficient to obtain the expected effect, and when the content exceeds the above range, the particles are used in an excessive amount, and thus it is not economically preferred.

Typically, a superabsorbent polymer has a hydrophilic surface, and because of capillary force, hydrogen bonding, polymeric inter-particular diffusion, or intermolecular Van der Waals force, resulting from water present between the particles upon drying after moisture absorption, an irreversible agglomeration may occur Therefore, since water is essentially used even in the polymerization and surface crosslinking process of the superabsorbent polymers, an agglomeration may occur and so an internal load may increase, and ultimately, it may be a cause of damaging the equipment. Further, since the agglomerated superabsorbent polymers have a large particle size, which are unsuitable for practical use, there is disadvantage in that a deagglomeration process has to be introduced so as to decrease the particle size to an appropriate size. Also, strong force is applied during the deagglomeration process, and thus, there existed a problem that the physical properties of the superabsorbent polymers could be deteriorated due to attrition of the superabsorbent polymers.

In order to solve these problems, attempts have been made to introduce a variety of fine particles, which are present on the surface of the superabsorbent polymer and can function to prevent direct agglomeration of the polymer particles. In the case where the fine particles were added in an excessive amount, agglomeration could be prevented, but there existed a disadvantage that the absorbency under pressure of the superabsorbent polymer was decreased.

To solve such problems, the particles introduced in the superabsorbent polymer of the present invention may have a particle size ranging from 2 nm to 50 μm. Further, the particles may have a BET specific surface area of 300 to 1500 $m^2/g$, preferably 500 to 1500 $m^2/g$, and more preferably 600 to 1500 $m^2/g$. Furthermore, the fine particles may have superhydrophobicity with a water contact angle of 125° or more, preferably 135° or more, and more preferably 140° or more. In addition, the particles may have a particle size ranging from 2 nm to 50 μm and superhydrophobicity with a water contact angle of 125° or more.

Moreover, the particles may have a porosity of 50% or more, and preferably 90% or more. As the attrition-resistant superabsorbent polymer uses the particles having the aforementioned features, it can reduce the effect of water present on the surface of the polymer, and further as fine particles having porous superhydrophobicity are used, the agglomeration may be remarkably reduced. In addition, even when a relatively small amount of fine particles is used, permeability may be easily increased, and the absorbency under pressure may be readily maintained.

The particles added in the method for preparing a superabsorbent polymer according to the present invention are not limited by its components as long as they are substances having the aforementioned features. Specifically, inorganic oxides, such as silica ($SiO_2$), alumina, titania ($TiO_2$) or carbon, inorganic compounds, organic polymers, ion exchange resins, metals, metal salts, and the like may be used, but are not limited thereto.

Further, as the process of adding the particles, a method of dispersing particles in a monomer solution, adding particles to a hydrogel polymer and then dry mixing them with primarily dried polymer particles, dispersing particles in water or an organic solvent in which a surface crosslinking agent is dissolved upon surface crosslinking, dry mixing particles separately from water or an organic solvent in which a surface crosslinking agent is dissolved upon surface crosslinking, or dry mixing particles with a surface-crosslinked product, etc. may be used, but is not limited thereto.

In another embodiment of the present invention, the water in the attrition-resistant superabsorbent polymer may be preferably contained in an amount of 0.1 to 20.0 parts by weight, more preferably 1.0 to 10.0 parts by weight, and most preferably 2.5 to 7.5 parts by weight based on 100 parts by weight of the superabsorbent polymer and the particles.

When the content of water is less than the above range, it may not be sufficient to obtain attrition resistance, and when the amount exceeds the above range, the surface stickiness of the polymer may be increased, and irreversible agglomeration between the superabsorbent polymer particles may occur, resulting in a decrease in processability of the polymer and changing the particle size at the same time, and thus, a problem may arise that it may not be suitably used as a product.

In the preparation process of a superabsorbent polymer, water is a polymerization medium, and is used in various applications, including facilitating the dispersion of the crosslinking solution during the surface crosslinking process, or the like. Further, residual moisture in the final product functions as an anti-static agent and a plasticizer for resin, and plays a role in suppressing the formation of very small superabsorbent polymer dust in the application process and preventing milling of the superabsorbent polymer particles. Generally, however, when water is added even in a small amount to the superabsorbent polymer, the surface stickiness of the polymer may be increased by the water absorbed on the surface thereof, and irreversible agglomeration of the superabsorbent polymer particles may occur. Such increase in stickiness and agglomeration may result in a decrease in processability such as a load increase in the preparation and application processes, consequently increasing the particle size of the superabsorbent polymer, deteriorating the physical properties thereof and decreasing productivity. Such superabsorbent polymers have been studied to date in terms of the polymerization process thereof and enhancements in absorption capacity thereby, and surface crosslinking for increasing the surface properties of the superabsorbent polymer or absorbency under pressure thereof. Furthermore, research is ongoing into changes in the surface properties of the superabsorbent polymer in order to solve some problems, such as to increase permeability or to prevent caking during storage of the superabsorbent polymer (anti-caking), etc.

In the present invention, water is additionally added to the superabsorbent polymer in the above range to increase the water content, and the water functions as a plasticizer to minimize the physical damage of the superabsorbent polymer, thereby simultaneously satisfying high water content and high processability, and thus, when water is added to the superabsorbent polymer, it becomes possible to uniformly contain water without caking phenomenon. Therefore, when the superabsorbent polymer is applied to the final products of diapers or the like, it is advantageous in that the deterioration of physical properties caused by physical attrition of the superabsorbent polymer, for example, by compression or strong air transfer during the production process of diapers, may be minimized.

In still another embodiment of the present invention, the organic acid is preferably contained in an amount of 0.001 to 5.0 parts by weight based on 100 parts by weight of the superabsorbent polymer, but is not limited thereto.

When the organic acid is contained in the above range, attrition resistance of the superabsorbent polymer is enhanced, and surface hydrophobicity of the superabsorbent polymer caused by containing the particles defined in the present invention can be reduced. In addition, it has an advantage in that a decrease in the absorbency under pressure (AUP) resulting from the use of the particles defined in the present invention can be minimized.

When the organic acid is contained in an amount exceeding the above range, surface stickiness of the superabsorbent polymer (SAP) occurs, and it may impose a negative influence on the particle size during post-treatment and thus is not economically preferable. Further, the anti-caking efficiency is greatly reduced. In contrast, when the organic acid is contained less than the above range, the desired effect cannot be achieved.

The organic acid may be at least one selected from the group consisting of citric acid, oxalic acid, acetic acid, malic acid, malonic acid, gluconic acid, ascorbic acid, tartaric acid, succinic acid, lactic acid, fumaric acid and salicylic acid. Citric acid is preferred because it is economical, safe and environmentally friendly, but is not limited thereto.

In one embodiment of the present invention, the polyhydric alcohol may be preferably contained in an amount of 0.01 to 5.0 parts by weight based on 100 parts by weight of the superabsorbent polymer, but is not limited thereto.

When the polyhydric alcohol is used, it is used together with water, which substantially reduces the amount of water contained in the superabsorbent polymer, thereby slightly decreasing the reduction of centrifuge retention capacity (CRC). Further, it may reduce absorption rate (measured vortex value) and may help to reduce hydrophobicity. Lastly, it has effects in increasing attrition resistance of the superabsorbent polymer and prolonging the retention period thereof.

When the polyhydric alcohol is contained in an amount exceeding the above range, a caking phenomenon, in which superabsorbent polymers are entangled or form an aggregate, may be induced. In contrast, when the polyhydric alcohol is contained less than the above range, the desired effect cannot be achieved.

The polyhydric alcohol may be at least one selected from the group consisting of propylene glycol, monoethylene glycol, diethylene glycol, triethylene glycol, tetraethylene glycol, polyethylene glycol, monopropylene glycol, 1,3-propanediol, dipropylene glycol, 2,3,4-trimethyl-1,3-pentanediol, polypropylene glycol, glycerol, polyglycerol, 2-butene-1,4-diol, 1,4-butanediol, 1,3-butanediol, 1,5-pentanediol, 1,6-hexanediol and 1,2-cyclohexanedimethanol. Propylene glycol is preferred because it is economical and safe, but is not limited thereto.

Detailed Description of the Embodiments

Hereinafter, the present invention will be described in more detail by way of non-limiting Examples. However, the embodiments of the present invention disclosed below are given for illustrative purposes only, and the scope of the present invention is not intended to be limited by these Examples. The scope of the present invention is given by the accompanying claims, and also contains all modifications within the meaning and range equivalent to the claims. Unless otherwise mentioned, "%" and "part", which indicate the amounts in the following Examples and Comparative Examples, are given on a mass basis.

EXAMPLES

Preparation Example: Preparation of Hydrogel Polymer 100 g of acrylic acid, 0.3 g of polyethylene glycol diacrylate as a crosslinking agent, 0.033 g of diphenyl(2,4,6-trimethylbenzoyl)-phosphine oxide as an initiator, 38.9 g of sodium hydroxide (NaOH), and 103.9 g of water were mixed to prepare a monomer mixture.

Thereafter, the monomer mixture was placed in a continuously moving conveyor belt and irradiated with UV rays (irradiation intensity: 2 $mW/cm^2$) to carry out UV polymerization for 2 minutes, thereby obtaining a hydrogel polymer.

Examples: Preparation of Superabsorbent Polymer

Example 1. Preparation of Superabsorbent Polymer Having Improved Attrition Resistance (1) The hydrogel polymer prepared according to the Preparation Example was cut into a size of 5*5 mm, dried in a hot air oven at 170° C. for 2 hours, milled using a pin mill to obtain a superabsorbent polymer having a particle size of 150 μm to 850 μm using a sieve.

(2) 0.025% by weight of Aerogel, namely, porous superhydrophobic fine particles (manufactured by JIOS), was added to the superabsorbent polymer based on 100% by weight of the superabsorbent polymer and stirred. Then, 0.064% by weight of citric acid and 0.64% by weight of aluminum sulfate were dissolved in 3.0% by weight of water, and then added to a stirrer.

Aerogel used had an average particle size of 5 μm, a BET specific surface area of 720 $m^2/g$, a water contact angle of 144°, and a porosity of 95%.

The particle sizes of Aerogel were measured and analyzed in accordance with the ISO 13320 by laser diffraction using a Helium-Neon Laser Optical System (HELOS). The BET specific surface area and the porosity were measured using a BET analyzer. The contact angle for water was measured using a contact angle analyzer (KRUSS DSA100). Specifically, a double-sided tape was applied onto a flat glass plate and then fine particles were coated thereon to a monolayer, and when 5 μl of ultrapure water was placed on the monolayer, the ultrapure water was placed in a drop form, and the angle formed between the water drop and the glass plate was repeatedly measured 4 times and then an average value was calculated.

Example 2. Preparation of Superabsorbent Polymer Having Improved Attrition Resistance A superabsorbent polymer was prepared in the same manner as in Example 1, except that 1.0% by weight of propylene glycol was further added in step (2) of Example 1.

Example 3. Preparation of Superabsorbent Polymer Having Improved Attrition Resistance A superabsorbent polymer was prepared in the same manner as in Example 1, except that 0.025% by weight of Aerogel, namely, porous superhydrophobic fine particles (manufactured by JIOS), was added to the superabsorbent polymer prepared in step (1) of Example 1 based on 100% by weight of the superabsorbent polymer and stirred, and 0.64% by weight of aluminum sulfate and 1.0% by weight of aluminum propylene glycol were dissolved in 3.0% by weight of water and then added to a stirrer.

Comparative Example 1. Preparation of Superabsorbent Polymer

A superabsorbent polymer was prepared in the same manner as in Example 1, except that step (2) of Example 1 was not carried out.

Comparative Example 2. Preparation of Superabsorbent Polymer

A superabsorbent polymer was prepared in the same manner as in Example 1, except that 0.025% by weight of Aerogel, namely, porous superhydrophobic fine particles (manufactured by JIOS), was added and stirred, and then 4% by weight of water (citric acid and aluminum sulfate were not added) was added in step (2) of Example 1.

Comparative Example 3. Preparation of Superabsorbent Polymer

A superabsorbent polymer was prepared in the same manner as in Example 1, except that citric acid was not added in step (2) of Example 1.

Reference Examples: Preparation of Superabsorbent Polymer to which Aerogel and Citric Acid are Added

Reference Example 1. Preparation of Superabsorbent Polymer

A superabsorbent polymer was prepared in the same manner as in Example 1, except that 0.025% by weight of aerogel, namely, porous superhydrophobic fine particles (manufactured by JIOS), was added to the superabsorbent polymer based on 100% by weight of the superabsorbent polymer and stirred, and 0.064% by weight of citric acid was dissolved in 3.0% by weight of water and then added to a stirrer in step (2) of Example 1.

Reference Example 2. Preparation of Superabsorbent Polymer

A superabsorbent polymer was prepared in the same manner as in Example 1, except that 0.025% by weight of Aerogel, namely, porous superhydrophobic fine particles (manufactured by JIOS), was added to the superabsorbent polymer based on 100% by weight of the superabsorbent polymer and stirred, and 0.160% by weight of citric acid was dissolved in 4% by weight of water and then added to a stirrer in step (2) of Example 1.

Reference Example 3. Preparation of Superabsorbent Polymer

A superabsorbent polymer was prepared in the same manner as in Example 1, except that 0.025% by weight of Aerogel, namely, porous superhydrophobic fine particles (manufactured by JIOS), was added to the superabsorbent polymer based on 100% by weight of the superabsorbent polymer and stirred, and 0.320% by weight of citric acid was dissolved in 4% by weight of water and then added to a stirrer in step (2) of Example 1.

Reference Example 4. Preparation of Superabsorbent Polymer

A superabsorbent polymer was prepared in the same manner as in Example 1, except that 0.025% by weight of Aerogel, namely, porous superhydrophobic fine particles (manufactured by JIOS), was added to the superabsorbent polymer based on 100% by weight of the superabsorbent polymer and stirred, and 1.0% by weight of propylene glycol was dissolved in 3.0% by weight of water and then added to a stirrer in step (2) of Example 1.

Reference Example 5. Preparation of Superabsorbent Polymer

A superabsorbent polymer was prepared in the same manner as in Example 1, except that Aerogel, namely, porous superhydrophobic fine particles (manufactured by JIOS), was not added to the superabsorbent polymer, and 0.64% by weight of aluminum sulfate was dissolved in 3.0% by weight of water based on 100% by weight of the superabsorbent polymer and then added to a stirrer in step (2) of Example 1.

Reference Example 6. Preparation of Superabsorbent Polymer

A superabsorbent polymer was prepared in the same manner as in Example 1, except that Aerogel, namely, porous superhydrophobic fine particles (manufactured by JIOS), was not added to the superabsorbent polymer, and 0.064% by weight of citric acid was dissolved in 1.0% by weight of propylene glycol based on 100% by weight of the superabsorbent polymer and then added to a stirrer in step (2) of Example 1.

Reference Example 7. Preparation of Superabsorbent Polymer

A superabsorbent polymer was prepared in the same manner as in Example 1, except that Aerogel, namely, porous superhydrophobic fine particles (manufactured by JIOS), was not added to the superabsorbent polymer, and 0.064% by weight of citric acid was dissolved in 3.0% by weight of water based on 100% by weight of the superabsorbent polymer and then added to a stirrer in step (2) of Example 1.

EXPERIMENTAL EXAMPLES

Figure 1:
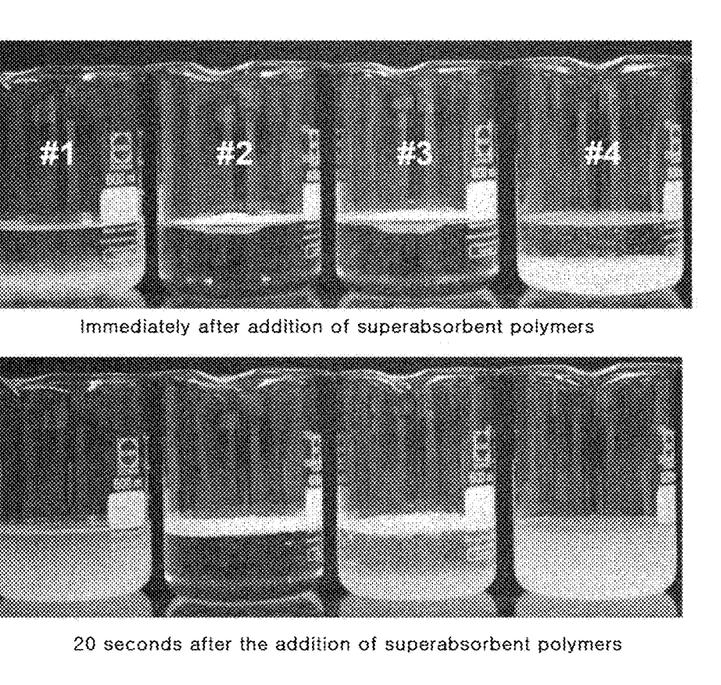
FIG. 1 shows the experimental results of Experimental Example 1 of the present invention.

Experimental Example 1. Test on the Presence or Absence of Hydrophobicity and Water Absorption The test was carried out in the following manner in order to simply determine the presence or absence of hydrophobicity of the superabsorbent polymers and water absorption, and the results are shown in FIG. 1.

After immersing 200 mL of deionized water (DI water) into a 600 mL beaker, 2 g of superabsorbent polymer (SAP)

was added simultaneously, and the change pattern was observed immediately after the addition and after 20 seconds of addition.

In the case of Comparative Example 2 (#2) and Comparative Example 3 (#3), the hydrophobic nature of Aerogel caused the superabsorbent polymers to float without being sank. In the case of Comparative Example 3 (#3), the addition of aluminum sulfate, which is a multivalent metal salt, caused the superabsorbent polymer to sink relatively quickly compared to the test of Comparative Example 2 (#2). In the case of Example 2 (#4), similar to the case of Comparative Example 1 (#1) in which no treatment was performed, the absorption behavior in which the superabsorbent polymer gradually swelled after sinking was exhibited even though it contained the Aerogel, thereby confirming that the hydrophobicity could be remarkably improved upon treatment with citric acid and propylene glycol.

Experimental Example 2-1. Attrition Resistance Test

The attrition resistance confirmation test was carried out by ball milling in order to simulate and confirm the degree of decrease in physical properties when the superabsorbent polymer was finally applied to a product.

10 pieces of alumina balls having a diameter of 2.5 cm and 20 g of the superabsorbent polymers prepared in Example 1 and Example 2 and Comparative Examples 1 to 3 were added to a jar having an internal diameter of 10 cm and subjected to ball milling under the condition of 300 rpm for 20 minutes. The results are shown as a change in particle size before and after ball milling (%), and are shown in Table 1 below.

TABLE 1

|  | Change in particle size before and after ball milling (%) |
| --- | --- |
| Example 1 | −9.0 |
| Example 2 | −5.8 |
| Example 3 | −6.4 |
| Comparative Example 1 | −17.5 |
| Comparative Example 2 | −10.0 |
| Comparative Example 3 | −10.7 |

The above results showed that the attrition resistance of the superabsorbent polymers of Example 2 and Example 3, which include at least three selected from the group consisting of Aerogel, citric acid, aluminum sulfate and propylene glycol, was significantly improved.

Experimental Example 2-2. Attrition Resistance Test

The attrition resistance test was carried out on the superabsorbent polymers prepared in Reference Examples 1 to 7, in which citric acid was added when preparing the superabsorbent polymers, in the same manner as in Experimental Example 2-1. The results are shown as a change in particle size before and after ball milling (%) and a water content (%), and are shown in Table 2 below

TABLE 2

|  | Change in particle size before and after ball milling (%) | Water content (%) |
| --- | --- | --- |
| Reference Example 1 | −11.5 | 4.4 |
| Reference Example 2 | −12.8 | 4.4 |
| Reference Example 3 | −11.2 | 4.4 |
| Reference Example 4 | −12.7 | 5.2 |
| Reference Example 5 | −9.3 | 4.9 |
| Reference Example 6 | −20.5 | 3.0 |
| Reference Example 7 | −10.9 | 4.8 |

Experimental Example 3. Centrifuge Retention Capacity (CRC)

The centrifuge retention capacity (CRC) was measured for each of the superabsorbent polymers prepared in Examples 1 to 3, Comparative Examples 1 to 3 and Reference Examples 1 to 7. The measurement of the centrifuge retention capacity was carried out in the following manner. After uniformly adding $W_0(g)$ (about 0.1 g) of each of the superabsorbent polymers in a nonwoven fabric-made bag and sealing the same, they were immersed in a 0.9 wt % physiological saline solution at room temperature. After 30 minutes; water was removed from the bag by centrifugation at 250 G for 3 minutes, and the weight $W_2(g)$ of the bag was then measured. Meanwhile, the same procedure was carried out without using the polymers, and then the resultant weight $W_1(g)$ was measured. Using the respective weights thus obtained, the centrifuge retention capacity (g/g) was determined according to the following Equation.

$CRC(g/g) = \{[W_2(g)-(g)]/W_0(g)\}-1$

The test results are shown in Table 3 below.

Experimental Example 4. Absorbency Under Pressure (AUP)

The absorbency under pressure (AUP) was measured for each of the superabsorbent polymers prepared in Examples 1 to 3, Comparative Examples 1 to 3 and Reference Examples 1 to 7. The absorbency under pressure was carried out in the following manner. A 400 stainless mesh was installed at the bottom of a plastic cylinder having an inner diameter of 60 mm. 0.90 g of each of the superabsorbent polymers prepared in Example 1 and Example 2 and Comparative Examples 1 to 3 were uniformly scattered on the mesh under conditions of room temperature and relative humidity of 50%. A piston which can further uniformly provide a load of 4.83 kPa (0.7 psi) was put thereon. The external diameter of the piston was slightly smaller than 60 mm, there was no gap between the cylindrical internal wall and the piston, and the jig-jog of the cylinder was not interrupted. At this time, the weight $W_a(g)$ of the device was measured. A glass filter having a diameter of 90 mm and a thickness of 5 mm was placed on a Petri dish having the diameter of 150 mm, and the physiological saline solution composed of 0.90 wt % sodium chloride was poured until the surface level became equal to the upper surface of the glass filter. Then, a sheet of filter paper having a diameter of 90 mm was put on the glass filter. Then, the measuring device was placed on the filter paper and the solution was absorbed under a load for about 1 hour. After one hour, the weight $W_b(g)$ of the device was measured after lifting the measuring device.

Then, the absorbency under pressure was calculated according to the following Equation from the weights of $W_a$ and $W_b$.

Absorbency under Pressure (g/g)=[$W_b$(g)−$W_a$(g)]/ Weight of Absorbed Polymer (g)

The test results are shown in Table 3.

Experimental Example 5. Absorption Rate

The absorption rate was measured for each of the superabsorbent polymers prepared in Examples 1 to 3, Comparative Examples 1 to 3 and Reference Examples 1 to 7. 50 mL of 0.9% saline and a magnetic bar having a size of 20*5 mm were added to a 100 mL beaker and stirred at 600 rpm. When a vortex is uniformly formed to an extent that the vortex is almost in contact with the magnetic bar, 2±0.01 g of the superabsorbent polymers prepared in Example 1 and Example 2 and Comparative Examples 1 to 3 were added to the formed vortex, and at this time, the time was measured simultaneously. The time measured until the vortex disappeared and thus the surface of the solution was completely level was defined as the absorption rate.

The test results are shown in Table 3.

Experimental Example 6. Permeability

The permeability was measured for each of the superabsorbent polymers prepared in Examples 1 to 3, Comparative Examples 1 to 3 and Reference Examples 1 to 7. About 10 mL of 0.9% saline was added to a cylinder having a diameter of 20 mm having a glass filter and a valve, and 0.2±0.0005 g of superabsorbent polymers classified into sizes of #30 to #50 were added. Thereafter, additional saline was added so that the total amount of 0.9% saline was 50 mL. After the superabsorbent polymers were sufficiently swollen for 30 minutes, the piston to which the mesh was attached was placed in the cylinder, and a pressure of 0.3 psi was applied. After 1 minute, the valve at the bottom of the cylinder was opened, and the time (in seconds) during which 20 mL of saline passed through the gel bed from the upper line to the lower line was measured.

The test results were shown in Table 4 below.

Experimental Example 7. Anti-Caking Efficiency

The anti-caking efficiency was measured for each of the superabsorbent polymers prepared in Examples 1 to 3, Comparative Examples 1 to 3 and Reference Examples 1 to 7. First, the weight of a Petri-dish having a diameter of 9 cm was measured and recorded (W1). Thereafter, 2±0.01 g of a sample was added to the Petri-dish in order to evenly distribute the sample. The Petri-dish was placed in a constant temperature and humidity chamber maintaining at a temperature of 40° C. and a humidity of 80% RH, and allowed to stand for 10 minutes. After 5 minutes, the weight of the polymer dropped on the floor was measured and recorded (S1). Then, the weight of the Petri-dish was measured and recorded (S2).

Anti-caking efficiency (%)=S1/((S2−W1)+S1)×100

TABLE 3

|  | Centrifuge retention capacity | Absorbency under pressure (AUP) | Absorption rate (sec) | Anti-caking Efficiency (%) |
|---|---|---|---|---|
| Example 1 | 31.4 | 18.4 | 69 | 100.0 |
| Example 2 | 31.8 | 16.4 | 75 | 100.0 |
| Example 3 | 30.8 | 16.4 | 68 | 100.0 |
| Comparative Example 1 | 32.8 | 18.6 | 81 | 0.0 |
| Comparative Example 2 | 31.6 | 17.3 | 83 | 0.0 |
| Comparative Example 3 | 31.9 | 16.7 | 71 | 100.0 |
| Reference Example 1 | 31.7 | 17.0 | 81 | 0.0 |
| Reference Example 2 | 32.1 | 17.2 | 83 | 0.0 |
| Reference Example 3 | 31.0 | 17.1 | 82 | 0.0 |
| Reference Example 4 | 31.6 | 17.7 | 92 | 0.0 |
| Reference Example 5 | 31.5 | 17.5 | 73 | 77.4 |
| Reference Example 6 | 31.8 | 18.8 | 89 | 0.0 |
| Reference Example 7 | 31.4 | 18.8 | 86 | 0.0 |

TABLE 4

|  | Permeability | |
|---|---|---|
|  | Before ball milling | After ball milling |
| Example 1 | 18 | 20 |
| Example 2 | 14 | 18 |
| Example 3 | 14 | 18 |
| Comparative Example 1 | 41 | 114 |
| Comparative Example 2 | 29 | 38 |
| Comparative Example 3 | 16 | 19 |
| Reference Example 1 | 55 | 44 |
| Reference Example 2 | 26 | 50 |
| Reference Example 3 | 27 | 43 |
| Reference Example 4 | 29 | 50 |
| Reference Example 5 | 15 | 22 |
| Reference Example 6 | 57 | 185 |
| Reference Example 7 | 51 | 74 |

Experimental Example 8. Measurement of Particle Size of Superabsorbent Polymer

The particle size was measured for each of the superabsorbent polymers prepared in Examples 1 to 3, Comparative Examples 1 to 3 and Reference Examples 1 to 7. The particle size was measured in accordance with EDANA recommended test method No. WSP 220.3. The superabsorbent polymers were classified into 850 μm, 600 μm, 300 μm, 150 μm and pan mesh, and were vibrated at an amplitude of 1.44 mm and a frequency of 50 Hz for 10 minutes, and then the content was measured as the residual amount at the upper portion of each sieve.

The measurement results are shown in Table 5 below.

TABLE 5

| | Particle size | | | | |
|---|---|---|---|---|---|
| | ~#20 | #20~#30 | #30~#50 | #50~#100 | #100~ |
| Example 1 | 0.43 | 32.80 | 53.86 | 12.09 | 0.82 |
| Example 2 | 0.42 | 27.81 | 54.06 | 16.09 | 1.62 |
| Example 3 | 0.29 | 22.92 | 56.45 | 18.48 | 1.86 |
| Comparative Example 1 | 0.56 | 31.31 | 54.24 | 12.50 | 1.40 |
| Comparative Example 2 | 0.94 | 36.46 | 53.84 | 8.41 | 0.35 |
| Comparative Example 3 | 0.43 | 27.70 | 53.96 | 16.27 | 1.64 |
| Reference Example 1 | 0.62 | 31.87 | 54.48 | 12.27 | 0.75 |
| Reference Example 2 | 0.73 | 29.73 | 56.20 | 12.61 | 0.74 |
| Reference Example 3 | 0.46 | 33.90 | 54.48 | 10.62 | 0.54 |
| Reference Example 4 | 3.81 | 40.91 | 48.36 | 6.62 | 0.30 |
| Reference Example 5 | 0.64 | 32.38 | 53.71 | 12.05 | 1.22 |
| Reference Example 6 | 0.45 | 29.53 | 59.01 | 11.01 | 0.00 |
| Reference Example 7 | 11.12 | 51.89 | 34.80 | 1.94 | 0.25 |

It can be confirmed from the results of Experimental Examples 1 to 8 that, the superabsorbent polymers prepared in Examples 1 to 3 showed no occurrence of fouling in the blender or lumps upon treatment with solution, compared to a conventional superabsorbent polymer. Further, although CRC and AUP were inevitably reduced as much as water was added, it was confirmed that the attrition resistance, permeability, absorption rate and anti-caking efficiency were improved.

The invention claimed is:

1. An attrition-resistant superabsorbent polymer, consisting of:
   a superabsorbent polymer having a crosslinked surface;
   water; and
   one of the following combinations:
   particles, a multivalent metal salt; and a polyhydric alcohol, or
   particles, an organic acid, and a polyhydric alcohol,
   wherein the particles have a BET specific surface area of 300 to 1500 $m^2/g$, and
   a porosity of 50% or more.

2. The attrition-resistant superabsorbent polymer of claim 1, wherein the particles are contained in an amount of 0.001 to 2.0 parts by weight based on 100 parts by weight of the superabsorbent polymer.

3. The attrition-resistant superabsorbent polymer of claim 1, wherein the water is contained in an amount of 1.0 to 10.0 parts by weight based on 100 parts by weight of the superabsorbent polymer and the particles.

4. The attrition-resistant superabsorbent polymer of claim 1, wherein the organic acid is contained in an amount of 0.001 to 5.0 parts by weight based on 100 parts by weight of the superabsorbent polymer.

5. The attrition-resistant superabsorbent polymer of claim 1, wherein the polyhydric alcohol is contained in an amount of 0.01 to 5.0 parts by weight based on 100 parts by weight of the superabsorbent polymer.

6. The attrition-resistant superabsorbent polymer of claim 1, wherein the organic acid is at least one selected from the group consisting of citric acid, oxalic acid, acetic acid, malic acid, malonic acid, gluconic acid, ascorbic acid, tartaric acid, succinic acid, lactic acid, fumaric acid and salicylic acid.

7. The attrition-resistant superabsorbent polymer of claim 1, wherein the polyhydric alcohol is at least one selected from the group consisting of propylene glycol, monoethylene glycol, diethylene glycol, triethylene glycol, tetraethylene glycol, polyethylene glycol, monopropylene glycol, 1,3-propanediol, dipropylene glycol, 2,3,4-trimethyl-1,3-pentanediol, polypropylene glycol, glycerol, polyglycerol, 2-butene-1,4-diol, 1,4-butanediol, 1,3-butanediol, 1,5-pentanediol, 1,6-hexanediol and 1,2-cyclohexanedimethanol.

8. The attrition-resistant superabsorbent polymer of claim 1, wherein the particles have a particle size ranging from 2 nm to 50 μm.

9. The attrition-resistant superabsorbent polymer of claim 1, wherein the particles have superhydrophobicity with a water contact angle of 125° or more.

10. The attrition-resistant superabsorbent polymer of claim 1, wherein the particles are at least one selected from the group consisting of silica ($SiO_2$), alumina, carbon and titania ($TiO_2$).

11. A method for preparing an attrition-resistant superabsorbent polymer comprising:
    adding only water, and one of the following combinations to a superabsorbent polymer having a crosslinked surface to prepare a attrition-resistant superabsorbent polymer, the combinations being:
    particles, a multivalent metal salt, and a polyhydric alcohol; or
    particles, an organic acid, and a polyhydric alcohol,
    wherein the particles
    having a BET specific surface area of 300 to 1500 $m^2/g$, and
    a porosity of 50% or more.

12. The method for preparing an attrition-resistant superabsorbent polymer of claim 11, wherein the particles are contained in an amount of 0.001 to 2.0 parts by weight based on 100 parts by weight of the superabsorbent polymer.

13. The method for preparing an attrition-resistant superabsorbent polymer of claim 11, wherein the water is contained in an amount of 1.0 to 10.0 parts by weight based on 100 parts by weight of the superabsorbent polymer and the particles.

14. The method for preparing an attrition-resistant superabsorbent polymer of claim 11, wherein the organic acid is contained in an amount of 0.001 to 5.0 parts by weight based on 100 parts by weight of the superabsorbent polymer.

15. The method for preparing an attrition-resistant superabsorbent polymer of claim 11, wherein the polyhydric alcohol is contained in an amount of 0.01 to 5.0 parts by weight based on 100 parts by weight of the superabsorbent polymer.

16. The method for preparing an attrition-resistant superabsorbent polymer of claim 11, wherein the organic acid is at least one selected from the group consisting of citric acid, oxalic acid, acetic acid, malic acid, malonic acid, gluconic acid, ascorbic acid, tartaric acid, succinic acid, lactic acid, fumaric acid and salicylic acid.

17. The method for preparing an attrition-resistant superabsorbent polymer of claim 11, wherein the polyhydric alcohol is at least one selected from the group consisting of propylene glycol, monoethylene glycol, diethylene glycol, triethylene glycol, tetraethylene glycol, polyethylene glycol, monopropylene glycol, 1,3-propanediol, dipropylene glycol, 2,3,4-trimethyl-1,3-pentanediol, polypropylene glycol, glycerol, polyglycerol, 2-butene-1,4-diol, 1,4-butanediol, 1,3-butanediol, 1,5-pentanediol, 1,6-hexanediol and 1,2-cyclohexanedimethanol.

18. The method for preparing an attrition-resistant superabsorbent polymer of claim 11, wherein the particles have a particle size ranging from 2 nm to 50 μm.

19. The method for preparing an attrition-resistant superabsorbent polymer of claim 11, wherein the particles have superhydrophobicity with a water contact angle of 125° or more.

20. The method for preparing an attrition-resistant superabsorbent polymer of claim 11, wherein the particles are at least one selected from the group consisting of silica ($SiO_2$), alumina, carbon and titania ($TiO_2$).

* * * * *